(12) United States Patent
Liu (10) Patent No.: US 8,470,787 B2
(45) Date of Patent: Jun. 25, 2013

(54) HYDRATES OF ERYTHROMYCIN SALTS, PREPARATION AND USE THEREOF

(76) Inventor: Li Liu, Foshan (CN)

( * ) Notice: Subject to any disclaimer, the term of this patent is extended or adjusted under 35 U.S.C. 154(b) by 147 days.

(21) Appl. No.: 13/003,397

(22) PCT Filed: Jul. 10, 2009

(86) PCT No.: PCT/CN2009/000787
§ 371 (c)(1),
(2), (4) Date: Apr. 1, 2011

(87) PCT Pub. No.: WO2010/003319
PCT Pub. Date: Jan. 14, 2010

(65) Prior Publication Data
US 2011/0184158 A1 Jul. 28, 2011

(30) Foreign Application Priority Data
Jul. 10, 2008 (CN) .................. 2008 1 0048383.4

(51) Int. Cl.
*A61K 31/70* (2006.01)
*C07H 17/08* (2006.01)
(52) U.S. Cl.
USPC ............................................. 514/29; 536/7.2
(58) Field of Classification Search
USPC ............................................. 536/7.2; 514/29
See application file for complete search history.

(56) References Cited

U.S. PATENT DOCUMENTS

| 5,658,887 A | * | 8/1997 | Gisby .............................. 514/29 |
| 6,268,489 B1 | | 7/2001 | Allen et al. |
| 2005/0119468 A1 | | 6/2005 | Kim et al. |

FOREIGN PATENT DOCUMENTS

| CN | 1030422 A | 1/1989 |
| CN | 1232037 A | 10/1999 |
| CN | 1625560 A | 6/2005 |
| EP | 0941999 A2 | 9/1999 |

OTHER PUBLICATIONS

International Search Report and Written Opinion mailed Oct. 22, 2009 (PCT/CN2009/000787): ISA/CN.

* cited by examiner

*Primary Examiner* — Elli Peselev
(74) *Attorney, Agent, or Firm* — Banner & Witcoff, Ltd.

(57) ABSTRACT

A macrolide derivative, i.e., a hydrate of erythromycin salts, has a molecular formula of $C_{37}H_{67}NO_{13}$.A.$nH_2O$, n=1.0-11.0, in which A is an organic acid or an organic acids, selected from lactobionic acid, thiocyanic acid, maleic acid, fumaric acid, thiocyanic acid, acetic acid, methanesulfonic acid, benzenesulfonic acid, nicotinic acid, lactic acid, citric acid, tartaric acid, aspartic acid, glutamic acid and phosphoric acid. The hydrate has better storage stability and is suitable for the manufacture of a medicament.

13 Claims, 7 Drawing Sheets

HYDRATES OF ERYTHROMYCIN SALTS, PREPARATION AND USE THEREOF

CROSS-REFERENCE TO RELATED APPLICATIONS/PRIORITY CLAIM

The present application is a U.S. National Phase filing of International Application No. PCT/CN2009/000787 filed on Jul. 10, 2009, designating the United States of America and claiming priority to China Patent Application No. 200810048383.4 filed on Jul. 10, 2008, both of which applications the present application claims priority to and the benefit of, and both of which applications are incorporated by reference herein in their entireties.

TECHNICAL FIELD

The present invention relates to the technical field of medicine, and specifically to the hydrates of salts of erythromycin, a macrolide derivative, preparation and use thereof.

BACKGROUND

Only erythromycin lactobionate [$C_{37}H_{67}NO_{13}.C_{12}H_{22}O_{12}$, CAS No.: 3847-29-8], erythromycin thiocyanate $C_{37}H_{67}NO_{13}.HCNS$, (CAS No.: 7704-67-8) and the like, and uses thereof have been reported in the prior art, but so far there is no published references that disclose a hydrate of salts of macrolide derivative erythromycin and preparation thereof.

CONTENTS OF THE INVENTION

In the first aspect, the present invention relates to a hydrate of erythromycin salts, characterized in that it has a molecular formula of $C_{37}H_{67}NO_{13}.A.nH_2O$, wherein n=1.0-11.0, for example, n is 1, 1.5, 2, 2.5, 3, 4, 4.5, 5, 5.5, 6, 6.2, 7, 8, 10, 11, and A is a pharmaceutically acceptable acid.

In the second aspect, the present invention relates to a pharmaceutical composition, comprising a hydrate of erythromycin salts according to the present invention and at least one pharmaceutically acceptable excipient.

In the third aspect, the present invention relates to a process for preparing a hydrate of erythromycin salts according to the present invention.

In the fourth aspect, the present invention relates to use of a hydrate of erythromycin salts according to the present invention in the manufacturing of a medicament, or a method for the treatment of diseases caused by bacteria, mycoplasma or chlamydia which is sensitive to erythromycin using a hydrate of erythromycin salts according to the present invention.

In one embodiment according to the first aspect, the invention provides a hydrate of erythromycin salts having a molecular formula of $C_{37}H_{67}NO_{13}.A.nH_2O$, n=1.0-11.0, A is a pharmaceutically acceptable acid, in which the pharmaceutically acceptable acid is lactobionic acid, thiocyanic acid, maleic acid, fumaric acid, thiocyanic acid, acetic acid, methanesulfonic acid, benzenesulfonic acid, nicotinic acid, lactic acid, citric acid, tartaric acid (including optically active tartaric acid and racemic tartaric acid), (including L-aspartic acid, D-aspartic acid, DL-aspartic acid), glutamic acid (including L-glutamic acid, D-glutamic acid, DL-glutamic acid) or phosphoric acid.

In another embodiment according to the first aspect, the invention provides a hydrate of erythromycin salts, which is erythromycin lactobionate undecahydrate.

In another embodiment according to the first aspect, the invention provides a hydrate of erythromycin salts, which is erythromycin lactobionate hexahydrate.

In another embodiment according to the first aspect, the invention provides a hydrate of erythromycin salts, which is erythromycin lactobionate pentahydrate.

In another embodiment according to the first aspect, the invention provides a hydrate of erythromycin salts, which is erythromycin lactobionate hemihepta(3.5)hydrate.

In another embodiment according to the first aspect, the invention provides a hydrate of erythromycin salts, which is erythromycin lactobionate trihydrate.

In another embodiment according to the first aspect, the invention provides a hydrate of erythromycin salts, which is erythromycin thiocyanate trihydrate.

In another embodiment according to the first aspect, the invention provides a hydrate of erythromycin salts, which is erythromycin thiocyanate dihydrate.

In another embodiment according to the first aspect, the invention provides a hydrate of erythromycin salts, which is erythromycin thiocyanate hemitri(1.5)hydrate.

In another embodiment according to the first aspect, the invention provides a hydrate of erythromycin salts, which is erythromycin phosphate hemipenta(2.5)hydrate.

The hydrates of erythromycin salts according to the present invention can be in different crystal forms, but in any cases, characteristically, when the hydrates of the present invention are dihydrated at an elevated temperature, their thermograms (TG-DTA/DSC) show apparent endothermic peaks, and their hygroscopicity is generally lower than that of the anhydrous. Some of the hydrates can be stably stored and have advantages of convenient for preparation or production of a solid formulation and aseptic filling of a formulation.

The results of water content as measured by Karl Fischer's method are consistent with those by the thermogravimetry. The thermogravimetric results demonstrate the following hydrates: crystalline 3-, 4-, 5-, 6-, undecahydrate of erythromycin lactobionate ($C_{38}H_{69}NO_{13}.C_{12}H_{22}O_{12}.3H_2O$, $C_{38}H_{69}NO_{13}.C_{12}H_{22}O_{12}.4H_2O$, $C_{38}H_{69}NO_{13}.C_{12}H_{22}O_{12}.5H_2O$, $C_{38}H_{69}NO_{13}.C_{12}H_{22}O_{12}.6H_2O$, $C_{38}H_{69}NO_{13}.C_{12}H_{22}O_{12}.11H_2O$) as well as crystalline hydrates of erythromycin thiocyanate (1.5-, 2-, 2.5-, 3-hydrate), and erythromycin phosphate hydrate including ($C_{38}H_{69}NO_{13}.H_3PO_4.2.5H_2O$).

In one embodiment according to the second aspect, the invention provides a pharmaceutical composition, comprising a hydrate of erythromycin salts according to the present invention, and at least one pharmaceutically acceptable excipient.

The pharmaceutical composition or medicament comprising a hydrate of erythromycin salts according to the present invention may be formulated to form a lyophilized powder injection, an aseptic filled powder injection, a small volume injection, a dosage form for intraenteral administration, an ointment and gel for percutaneous administration, effervescent tablets, or a suppository for intravaginal or rectal administration.

In one embodiment according to the third aspect, the invention provides a process for preparing a hydrate of erythromycin salts according to the present invention, comprising:

Method A: in a reaction container, using one of chloroform, $C_3$-$C_6$ ketone, $C_2$-$C_6$ ester, water and $C_1$-$C_5$ alcohol or a mixture thereof as solvent, adding erythromycin, stirring, adding an organic acid, then adding one or more of $C_3$-$C_6$ ketone, chloroform, $C_1$-$C_5$ alcohol, $C_2$-$C_6$ ether, $C_2$-$C_6$ ester and benzene after complete reaction, cooling, filtering, washing the resultant solid with one or more of organic solvents $C_1$-$C_5$ alcohol, $C_3$-$C_6$ ketone, $C_2$-$C_6$ ether and chloroform, filtering under a reduced pressure, and drying to obtain the hydrate of erythromycin salts; or Method B: adding a solution of a pharmaceutically acceptable acid in a desired molar ratio to a reaction container containing erythromycin and one or more of water, $C_1$-$C_5$ alcohol and $C_3$-$C_6$ ketone as the solvent(s), stirring, maintaining at a temperature between −10° C. and 30° C. for 0.5-24 h, decoloring with activated carbon or filtering with an ultrafilter membrane, cooling to a temperature between −70° C. and −30° C., and drying under vacuum to obtain the hydrates of erythromycin salts; or Method C: adding a pharmaceutically acceptable acid or a solution thereof in a desired molar ratio to a reaction container containing erythromycin and water, stirring, maintaining at a temperature between −5° C. and 20° C. for 0.5-24 h, decoloring with activated carbon or filtering with an ultrafilter membrane, and spray drying to obtain the hydrates of erythromycin salts.

In one embodiment according to the fourth aspect, the invention provides use of a hydrate of erythromycin salts according to the present invention in the manufacture of a medicament, wherein the medicament is useful in the treatment of an infection in a human or an animal caused by bacteria, mycoplasma or chlamydia which is sensitive to erythromycin.

In another embodiment according to the fourth aspect, the invention provides a method for the treatment of an infection in a human or an animal caused by bacteria, mycoplasma or chlamydia which is sensitive to erythromycin using a hydrate of erythromycin salts according to the present invention.

The inventors of the present invention have found by studying that the hydrates of erythromycin salts according to the present invention have surprising technical effects. Specifically, the hydrates of erythromycin salts according to the present invention have hygroscopicity (moisture absorption) generally lower than that of the corresponding anhydrous and usually are stable. For example, unlike erythromycin that is sparingly soluble in water and erythromycin lactobionate anhydrous that is more hygroscopic, erythromycin lactobionate having crystal water and the like is soluble in water, has a good stability during storage at room temperature, convenient for preparing a freely soluble and absorptive formulation, and convenient for storage and transportation. In addition, the anhydrous can be moisturized so that it must be treated under the isolation of air to avoid adhering, while the hydrates have a good flow property which improves the processing of formulation and facilitates preparation of a pharmaceutical formulation.

The hydrates of erythromycin salts according to the present invention can be stably stored. A sample of the above hydrates was sealed in a vial, and an accelerated stability test was conducted at 30° C. and changes of the content and related substances were measured by a HPLC method (C18 reverse phase column, 0.01M $KH_2PO_4$-acetonitrile (60:40) as the mobile phase, detective wavelength: 215 nm, column temperature: 35° C., flow rate: 1.0 ml/min) (upon different hydrates of erythromycin salts, such as crystalline hydrates of erythromycin thiocyanate, the pH of the mobile phase can be adjusted and $KH_2PO_4$ can be changed into $NaH_2PO_4$, the detective wavelength can be changed into 210 nm, and the column temperature can be set at 35-55° C., such as 50° C. for analysis and measurement). Surprisingly, the content and the related substances of the hydrates of organic acid salts of erythromycin according to the present invention show no significant change. According to China Pharmacopeia CP2005, a 5 g sample of the hydrate of erythromycin salts was tested in a hygroscopic test at 25° C. and a relative humidity of 75%, and it was surprisingly found that the hydrates of organic acid salts of the present invention had a relatively small proportion of weight gain caused by moisture absorption. As compared to the anhydrous of erythromycin salt, the hydrates of erythromycin salts according to the present invention have a lower hygroscopicity, i.e., has a better stability of hygroscopicity, which facilitates the package and storage thereof, or is a more advantageously stable form for storage relative to the anhydrous. The results are shown in the following tables.

TABLE 1

Results of the accelerated stability test for erythromycin lactobionate hexahydrate

| Sampling time (Month) | Form | Assay (%) |
|---|---|---|
| 0 | off-white powder | 99.7 |
| 1 | off-white powder | 99.6 |
| 2 | off-white powder | 100.2 |
| 3 | off-white powder | 99.8 |
| 6 | off-white powder | 99.6 |

TABLE 2

Results of the accelerated stability test for erythromycin lactobionate pentahydrate

| Sampling time (Month) | Form | Assay (%) |
|---|---|---|
| 0 | off-white powder | 99.9 |
| 1 | off-white powder | 100.2 |
| 2 | off-white powder | 99.8 |
| 3 | off-white powder | 100.1 |
| 6 | off-white powder | 99.9 |

TABLE 3

Results of the accelerated stability test for erythromycin lactobionate trihydrate

| Sampling time (Month) | Form | Assay (%) |
|---|---|---|
| 0 | off-white powder | 99.9 |
| 1 | off-white powder | 100.2 |
| 2 | off-white powder | 99.8 |
| 3 | off-white powder | 100.1 |
| 6 | off-white powder | 99.9 |

TABLE 4

Results of the accelerated stability test for erythromycin thiocyanate trihydrate

| Sampling time (Month) | Form | Assay (%) |
|---|---|---|
| 0 | off-white powder | 99.8 |
| 1 | off-white powder | 99.9 |
| 2 | off-white powder | 100.6 |
| 3 | off-white powder | 100.3 |
| 6 | off-white powder | 100.1 |

TABLE 5

Results of the accelerated stability test
for erythromycin thiocyanate dihydrate

| Sampling time (Month) | Form | Assay (%) |
|---|---|---|
| 0 | off-white powder | 99.9 |
| 1 | off-white powder | 99.9 |
| 2 | off-white powder | 100.4 |
| 3 | off-white powder | 100.2 |
| 6 | off-white powder | 99.8 |

TABLE 6

Results of the accelerated stability test for
erythromycin thiocyanate hemitri(1.5)hydrate

| Sampling time (Month) | Form | Assay (%) |
|---|---|---|
| 0 | off-white powder | 99.9 |
| 1 | off-white powder | 100.3 |
| 2 | off-white powder | 100.5 |
| 3 | off-white powder | 100.1 |
| 6 | off-white powder | 100.2 |

TABLE 7

Results of the hygroscopic test for the organic
acid salts of erythromycin (RH 75%, 25° C.)

| Sampling time (48 h) | Hygroscopic weight gain %, relative to 0 h |
|---|---|
| Erythromycin lactobionate undecahydrate | 0.04% |
| Erythromycin lactobionate hexahydrate | 7.31% |
| Erythromycin lactobionate pentahydrate | 8.93% |
| Erythromycin lactobionate tetrahydrate | 10.12% |
| Erythromycin lactobionate trihydrate | 12.07% |
| Erythromycin lactobionate anhydrous | 17.86% |

TABLE 8

Results of the hygroscopic test of the organic
acid salts of erythromycin (RH 75%, 25° C.)

| Sampling time (48 h) | Hygroscopic weight gain %, relative to 0 h |
|---|---|
| Erythromycin thiocyanate trihydrate | 0.02% |
| Erythromycin thiocyanate dihydrate | 2.03% |
| Erythromycin thiocyanate hemitri(1.5) hydrate | 3.12% |
| Erythromycin thiocyanate anhydrous | 6.75% |

The hydrates of erythromycin salts are dissolved in water or ethanol aqueous solution, then $NaHCO_3$ or $Na_2CO_3$ or ammonia or other basic solution is added, the obtained precipitate is filtered, washed with water, and recrystallized with one or more of water or methanol, ethanol or acetone. The resultant crystal is consistent with erythromycin in terms of specific rotation, MS and the like data or spectra.

The hydrates of erythromycin salts according to the present invention can be used for the preparation or purification of erythromycin, for the preparation of erythromycin oxime, for the further synthesis of intermediates of macrolides such as roxithromycin, clarithromycin, azithromycin, dirithromycin, bridged erythromycin, cethromycin, and of medicaments thereof.

The tablets, capsules, powders, pulvis, premix, soluble powder, granules for the preparation of dosage forms for enteral administration can comprise pharmaceutically acceptable a filler, such as starch, modified starch, lactose, microcrystalline cellulose, cyclodextrin, sorbitol, mannitol, calcium phosphate, amino acids; pharmaceutically acceptable disintegrating agent, such as starch, modified starch, microcrystalline cellulose, sodium carboxymethyl starch, cross-linked polyvinylpyrrolidinone, low-substituted hydroxypropyl cellulose, surfactants; pharmaceutically acceptable wetting agent and adhesive, such as pregelatinized starch, methylcellulose, sodium carboxymethylcellulose, ethylcellulose, polyvinylpyrrolidinone, alginic acid and salts thereof; pharmaceutically acceptable lubricant and flow aid, such as stearic acid, magnesium stearate, polyethylene glycol 4,000-6,000, talc powder, micronized silica gel, magnesium laurylsulfate; pharmaceutically acceptable sweeteners and flavoring agents, such as aspartame, sodium cyclamate, saccharin sodium, sucrose, and edible flavor.

The hydrates of the present invention are different from erythromycin that is sparingly soluble in water, so that the dissolution rate of solid dosage form thereof is significantly influenced by the formulation process. The hydrates of erythromycin salts of organic acids or inorganic acids are freely soluble in water, so that the solid dosage forms thereof have good dissolubility, can be readily absorbed and enter blood circulation, have an improved bioavailability and facilitate the rapid onset of their antibacterial effects.

The premix of the hydrate of erythromycin salts according to the present invention can be obtained by mixing hydrate with animal-acceptable drugs or feeds (including corn feeds), feed additives (including amino acids, vitamins, flavoring essences), binding agents. The pulvis or soluble powder of the hydrate of erythromycin salts according to the present invention can be prepared by convention process and equipment with other pharmaceutically acceptable fillers, disintegrating agents, wetting agents and binding agents.

The suppository and gel according to the present invention are different from erythromycin suppository or ointment. Since erythromycin is sparingly soluble in water, an oil soluble excipient is usually added, which may easily cause contamination that can hardly be cleaned. However, the hydrates of erythromycin salts are more soluble in water, so that the suppository and gel thereof have a good release property, can be readily absorbed and enter into blood circulation, thereby having an improved bioavailability, facilitating the rapid onset of the antibacterial effects. Since no oil soluble excipient is needed, a contamination is normally not caused and can be readily cleaned.

The suppository of the hydrates of erythromycin salts: consist of a hydrate of erythromycin salts 5-50%, and suppository base 50-95%, in which the base may be ethanol, glycerol, glycerol gelatine, polyethylene glycol 200-8,000, poloxamer, semi-synthetic fatty acid esters, Carbomer (931, 934, 940, 974, AA-1, 1342, etc.), and Tween 60-80. Preparation method: mixing the active ingredient with the base, heating in a water bath, stirring, melting, stirring uniformly, rapidly pouring into a suppository mould coated with a lubricant until slightly overflowing the suppository mould, cooling and smoothing, and removing the mould to obtain the suppository.

Methods for preparing the gel of hydrates of erythromycin salts: uniformly mixing a hydrate of erythromycin salts (charging in an amount based on erythromycin) with 50-95% of bases, in which the base can be ethanol, glycerol, triethanolamine, glycerol gelatine, polyethylene glycol 200-8,000, poloxamer, polyvinylpyrrolidinone, semi-synthetic fatty acid ester, water-soluble monoglyceride, Carbomer (931, 934, 940, 974, AA-1, 1342, etc.), and Tween 60-80. The gel may comprise a pharmaceutically acceptable preservative and stabilizing agent. When formulating, Carbomer can be dispersed in water, then glycerol and polyethylene glycol 200-8,000 are added, heated, stirred and mixed, a prescribed amount of a hydrate of erythromycin lactobionate is added, stirred, a pharmaceutically acceptable inorganic or organic base is added to adjust the pH to about 5.0-7.0, and then water is added to the full volume. The mixture is stirred uniformly and filled to obtain the gel.

Methods for preparing the lyophilized powder injection: a hydrate of organic acid salts of erythromycin (in an amount based on erythromycin) and optional pharmaceutically acceptable lyophilizing supporter or excipient are dissolved in water for injection, a pharmaceutically acceptable acid/base is added to reach a pH of 5.0-7.5, if necessary, 0.005-0.5% (WN) of activated carbon is added and stirred for 15-45 min, filtered, and the filtrate is supplemented with water, filtrated under aseptic condition, filled in 25-250 mg/bottle (based on the active ingredient), lyophilized, and plugged to obtain the product.

Methods for preparing a small volume injection of the hydrates of organic acid salts of erythromycin: a hydrate of organic acid salts of erythromycin is mixed with water for injection and pharmaceutically acceptable additives such as pharmaceutically acceptable pH regulating agent, pharmaceutically acceptable antioxidant, inert gases, then filtered, and the filtrate is sterilized to obtain the small volume injection having a pH of 5.0-7.5.

The pharmaceutically acceptable pH regulating agent can be a pharmaceutically acceptable inorganic or organic acid, inorganic or organic base, as well as a general Lewis acid or base, and may be one or more selected from a group consisting of hydrochloric acid, phosphoric acid, propionic acid, acetic acid and acetic acid salts, such as sodium acetate, lactic acid and pharmaceutically acceptable lactates, pharmaceutically acceptable citrates, sodium carbonate, sodium hydrogen carbonate, sodium hydroxide, potassium hydroxide, phosphates, tartaric acid and pharmaceutically acceptable salts thereof, sodium borate, boric acid, succinic acid, caproic acid, adipic acid, fumaric acid, maleic acid, trihydroxyamiomethane, diethanolamine, ethanolamine, isopropanolamine, diisopropanolamine, 2-amino-2-(hydroxymethyl) 1,3-propan-1,3-diol-amine, hexane-1,2-diamine, N-methyl glucamine, diisopropylamine and salts thereof; polyhydroxy carboxylic acid and salts thereof, such as glucuronic acid, gluconic acid, lactobionic acid, malic acid, threonic acid, glucoheptonic acid, amino acids and salts of amino acids.

The pharmaceutically acceptable antioxidant and stabilizer may be one or more of sulfinic acid, sulfites, hydrosulfites, pyrosulfites, hyposulfites, thiosulfate, organosulfur compound such as thiourea, glutathione, dimercaptopropanol, thioglycollic acid and salts thereof, thiolactic acid and salts thereof, thiodipropionic acid and salts thereof, phenol compounds such as gallic acid and salts thereof, caffeic acid, caffeates, ferulic acid, ferulates, di-tert-butyl-p-phenol, 2,5-dihydroxybenzoic acid, 2,5-dihydroxybenzoate, phenol and derivatives, salicylic acid and salts thereof; amino acids and salts thereof ascorbic acid and ascorbates, isoascorbic acid and isoascorbates, nicotinamide, tartaric acid, nitrates, phosphates, pharmaceutically acceptable acetates, citrates, EDTA and EDTA salts such as disodium EDTA, tetrasodium EDTA, N-di(2-hydroxyethyl)glycine.

The pharmaceutically acceptable isotonic regulating agent may be one or more of glucose, fructose, xylitol, sorbitol, mannitol, invertose, maltose, dextran, sodium chloride, potassium chloride, sodium lactate.

The method for removing pyrogens and bacteria can comprise: adding 0.005-3% of activated carbon to remove pyrogens, using micropore filter to remove bacteria and using an autoclaves sterilizer, as well as using ultrafilter to remove bacteria and pyrogens. By ultrafiltration, the used ultrafilter can be in form of plate, roll, tube, hollow fiber or round box, preferably in form of roll and hollow fiber. After most of heat generation substances and bacteria are removed by using a filtration membrane having a relative molecular weight cut-off of 50,000-300,000, then the residual pyrogens are removed by using an ultrafilter membrane having a relative molecular weight cut-off of 4,000-60,000, preferably an ultrafilter membrane having a relative molecular weight cut-off of 6,000-30,000.

The hydrates of erythromycin lactate can be used for preparing erythromycin base or other organic acid salts of erythromycin or hydrates thereof in high quality; the hydrate of erythromycin thiocyanate can be used for preparing erythromycin base or erythromycin oxime or erythromycin A oxime or salts thereof. The erythromycin oxime or salts thereof can be further used for synthesizing intermediates and medicaments of macrolides such as roxithromycin, clarithromycin, azithromycin, dirithromycin, bridged erythromycin, cethromycin. For example, the hydrate of erythromycin thiocyanate, hydroxyamine or hydroxyamine hydrochloride, sodium hydroxide or ammonium hydrogen carbonate or other Lewis bases or aqueous solution thereof, methanol or isopropanol are added to a reaction bottle, reaction with stirring at about 20-60° C. for 6-72 h, cooled down to 20° C. or below, filtered, the filter cake is added to isopropanol or acetone and adjusted with ammonia or sodium carbonate or NaOH solution to reach a pH of 9.5-12, stirred, cooled to precipitate a precipitate, which is filter out to obtain erythromycin oxime.

The antibacterial activities of the hydrates of erythromycin salts are determined by culturing clinically obtained bacteria and measuring in accordance with pharmacological test methods (the tube double dilution method), and the results are shown in the following tables 9, 10, 11 and 12.

TABLE 9

Antibacterial activity of erythromycin lactobionate hexahydrate MIC (mg/L)

| Bacteria for infection | Strains | MIC (mg/L) | | |
|---|---|---|---|---|
| | | MIC | $MIC_{50}$ | $MIC_{90}$ |
| Staphylococcus aureus | 26 | 0.06-128 | 0.12 | 128 |
| Staphylococcus epidermidis | 21 | 0.12-128 | 16 | 128 |
| Pneumococcus | 18 | 0.03-0.5 | 0.06 | 1 |
| Streptococcus viridan | 23 | 0.03-128 | 0.06 | 0.5 |
| Streptococcus hemolyticus | 16 | 0.03-32 | 0.06 | 32 |
| Neisseria gonorrhoeae | 16 | 0.06-2 | 0.25 | 1 |
| Bacillus influenzae | 17 | 0.12-8 | 4 | 8 |
| Escherichia coli | 21 | 0.5-128 | 4 | 128 |
| Bacillus fragilis | 15 | 0.5-64 | 4 | 16 |
| Shigella | 25 | 0.12-128 | 128 | 128 |
| Propionibacterium | 18 | 0.03-16 | 0.06 | 0.12 |
| Anaerobe | 16 | 0.06-64 | 2 | 16 |

TABLE 10

Antibacterial activity of erythromycin
lactobionate pentahydrate MIC (mg/L)

| Bacteria for infection | Strains | MIC (mg/L) | | |
|---|---|---|---|---|
| | | MIC | $MIC_{50}$ | $MIC_{90}$ |
| Staphylococcus aureus | 26 | 0.06-128 | 0.12 | 128 |
| Staphylococcus epidermidis | 21 | 0.12-128 | 16 | 128 |
| Pneumococcus | 18 | 0.03-0.5 | 0.06 | 1 |
| Streptococcus viridan | 23 | 0.03-128 | 0.06 | 0.5 |
| Streptococcus hemolyticus | 16 | 0.03-32 | 0.06 | 32 |
| Neisseria gonorrhoeae | 16 | 0.06-2 | 0.25 | 1 |
| Bacillus influenzae | 17 | 0.12-8 | 4 | 8 |
| Escherichia coli | 21 | 0.5-128 | 4 | 128 |
| Bacillus fragilis | 15 | 0.5-64 | 4 | 16 |
| Shigella | 25 | 0.12-128 | 128 | 128 |
| Propionibacterium | 18 | 0.03-16 | 0.06 | 0.12 |

TABLE 11

Antibacterial activity of erythromycin
lactobionate trihydrate MIC (mg/L)

| Bacteria for infection | Strains | MIC (mg/L) | | |
|---|---|---|---|---|
| | | MIC | $MIC_{50}$ | $MIC_{90}$ |
| Staphylococcus aureus | 26 | 0.06-128 | 0.12 | 128 |
| Staphylococcus epidermidis | 21 | 0.6-128 | 16 | 128 |
| Pneumococcus | 18 | 0.03-0.5 | 0.06 | 1 |
| Streptococcus viridan | 23 | 0.03-128 | 0.06 | 0.5 |
| Streptococcus hemolyticus | 16 | 0.03-32 | 0.06 | 32 |
| Neisseria gonorrhoeae | 16 | 0.06-2 | 0.25 | 1 |
| Bacillus influenzae | 17 | 0.12-8 | 4 | 8 |
| Escherichia coli | 21 | 0.5-128 | 4 | 128 |
| Bacillus fragilis | 15 | 0.5-64 | 4 | 16 |
| Shigella | 25 | 0.12-128 | 128 | 128 |
| Propionibacterium | 18 | 0.03-16 | 0.06 | 0.12 |

TABLE 12

Antibacterial activity of erythromycin
thiocyanate dehydrate MIC (mg/L)

| Bacteria for infection | Strains | MIC (mg/L) | | |
|---|---|---|---|---|
| | | MIC | $MIC_{50}$ | $MIC_{90}$ |
| Staphylococcus aureus | 26 | 0.03-128 | 0.12 | 128 |
| Staphylococcus epidermidis | 21 | 0.6-128 | 16 | 128 |
| Pneumococcus | 18 | 0.03-0.5 | 0.06 | 1 |
| Streptococcus viridan | 23 | 0.03-128 | 0.06 | 0.5 |
| Streptococcus hemolyticus | 16 | 0.03-32 | 0.06 | 32 |
| Neisseria gonorrhoeae | 16 | 0.06-2 | 0.25 | 1 |
| Bacillus influenzae | 17 | 0.12-8 | 4 | 8 |
| Escherichia coli | 21 | 0.5-128 | 4 | 128 |
| Bacillus fragilis | 15 | 0.5-64 | 4 | 16 |
| Shigella | 25 | 0.12-128 | 128 | 128 |
| Propionibacterium | 18 | 0.03-16 | 0.06 | 0.12 |
| Anaerobe | 16 | 0.06-64 | 2 | 16 |

Clinical Applications of the Hydrates of Erythromycin Salts According to the Present Invention The hydrates of salts of the macrolide derivative erythromycin of the present invention, as antibacterial drugs, have a broad spectrum of antibacterial activities, and are useful in medicaments for the treatment or prophylaxis of infections in a human and an animal caused by bacteria, mycoplasma, or chlamydia sensitive to erythromycin, which infections include: A. infections of nasopharynx: tonsillitis, pharyngitis, sinustitis; B. infections of lower respiratory duct: acute bronchitis, acute onset of chronic bronchitis, and pneumonia; C. infections of skin and soft tissues: impetigo, erysipelas, folliculitis, furnucle and wound infections; D. acute otitis, mycoplasmal pneumonia, urethritis and cervicitis caused by *chlamydia trachomatis*; and *E. legionella* infections, *mycobacterium avium* infections, *helicobacter pylori* infections.

In general, for an animal or a human with a body weight of 10-70 kg, intramuscular injection: 25-500 mg (based on erythromycin); intravenous administration: mixing 25-500 mg (based on erythromycin) of the injection of the present invention in 50-500 ml of 0.9% NaCl solution for transfusion or 5% glucose solution, intravenous injection, 1-2 times per day.

Dose and usage for oral administration (based on erythromycin): for an animal or a human with a body weight of 10-70 kg, in general, 50-500 mg/day, once per 6-8 h.

Dose and usage for suppository (based on erythromycin): in general, 50-500 mg/day.

CONCRETE MODES FOR CARRYING OUR THE INVENTION

The following examples are provided to further illustrate the present invention, but are not intended to limit the present invention to these examples in any way.

Example 1

Preparation of Erythromycin Lactobionate Undecahydrate

Figure 1:
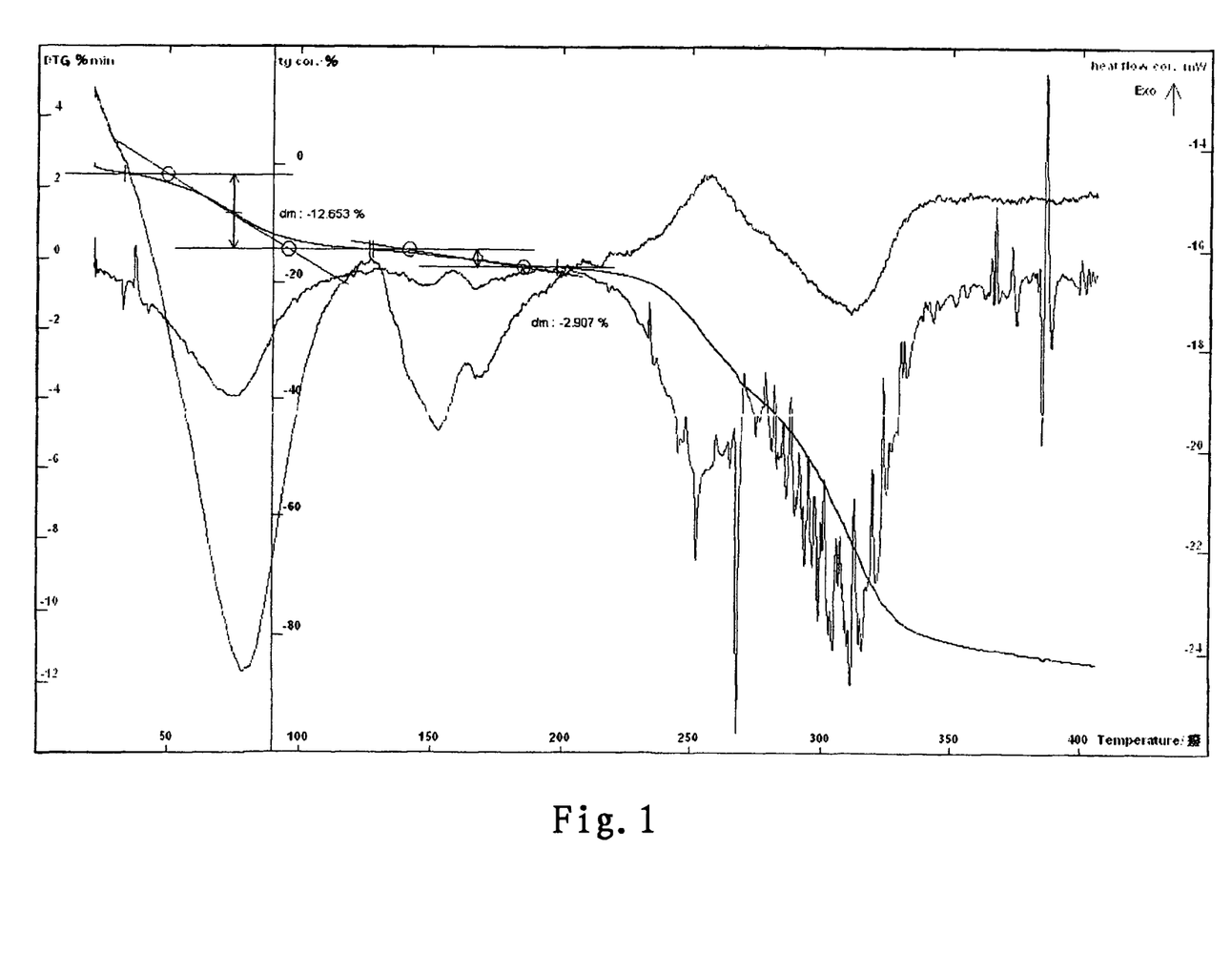
FIG. 1 is a thermogram of erythromycin lactobionate undecahydrate.

In a three-necked flask, 50 ml of acetone and 8 g erythromycin were added, stirred, lactobionic acid or an aqueous solution thereof was added, and stirred at 5-35° C. After complete reaction, anhydrous acetone was added slowly, and the mixture was cooled to about −30-5° C. After a solid was precipitated and filtered out, the solid was washed with anhydrous acetone, and filtered under a reduced pressure to obtain an off-white crystal powder, which was very freely soluble in water. HPLC: the main peak of the sample shows a retention time in consistent with that of erythromycin control, in which the content of erythromycin was 56.79% (56.88%); melting point: 95.1-116.3° C. (not corrected), water content by Karl Fischer method was 15.53% (the theoretical value: 15.36%), TG: weight loss at platform before 200° C. was about 15.56% (see FIG. 1), MS (ESI) m/z: 1092, 734, 358. Element analysis: found: C, 45.73; H, 8.54; N, 1.15; theoretical values: C, 45.61; H, 8.67; N, 1.09.

Example 2

Preparation of Erythromycin Lactobionate Hexahydrate

Figure 2:
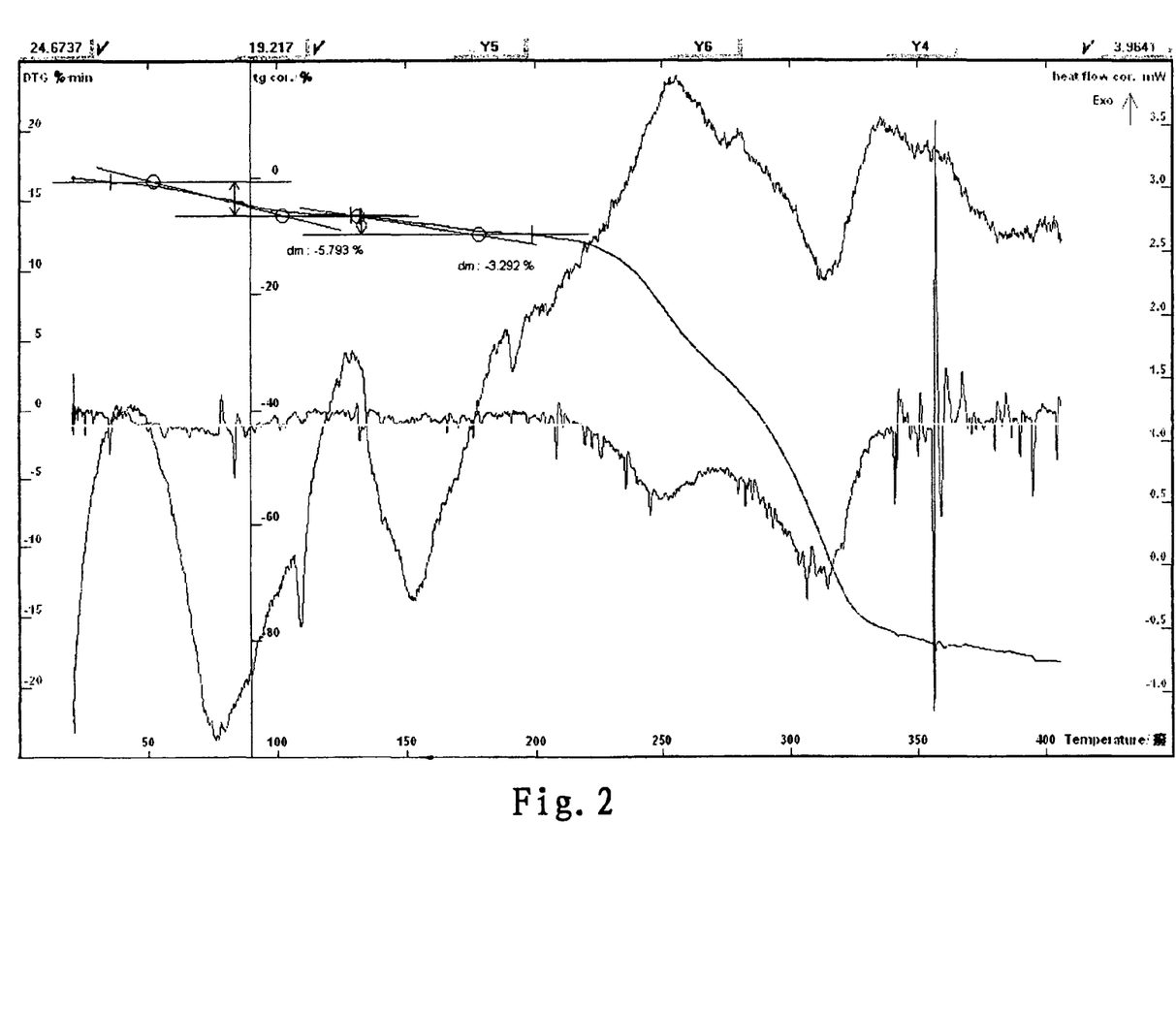
FIG. 2 is a thermogram of erythromycin lactobionate hexahydrate.

In a three-necked flask, 50 ml of acetone and 10 g erythromycin were added, equimolar lactobionic acid or a solution thereof in acetone-water was added at 10-40° C. with stirring, and reaction was performed for 0.2-4 h. After complete reaction, anhydrous acetone in 1-8 times was added slowly. The mixture was cooled to a temperature of −45° C. to −10° C., filtered, the resultant solid was washed with acetone, filtered under a reduced pressure and dried at about 80° C. to obtain an off-white powder, which was very freely soluble in water. HPLC: the main peak of the sample had a retention time in consistent with that of erythromycin control, in which the content of erythromycin was 61.91% (the theoretical value: 62.08%); melting point: 132.6-137.7° C. (not corrected); water content (by Karl Fischer method): 9.16%, TG: weight loss at platform before 200° C. was about 9.09% (the theoretical value: 9.01%) (see FIG. 2), MS (ESI, FAB) m/z: 1092, 1091, 734, 733, 358, 357; Element analysis: found: C, 49.11; H, 8.55; N, 1.21; calculated: C, 49.03; H, 8.48; N, 1.17. The obtained sample was dissolved in water, added with a saturated $Na_2CO_3$ solution to produce a precipitate, the precipitate was filtered out, washed with water, recrystallized from water-ethanol, and the product was consistent with raw material erythromycin in terms of specific optical rotation and MS data.

Example 3

Preparation of Erythromycin Lactobionate Trihydrate

Figure 4:
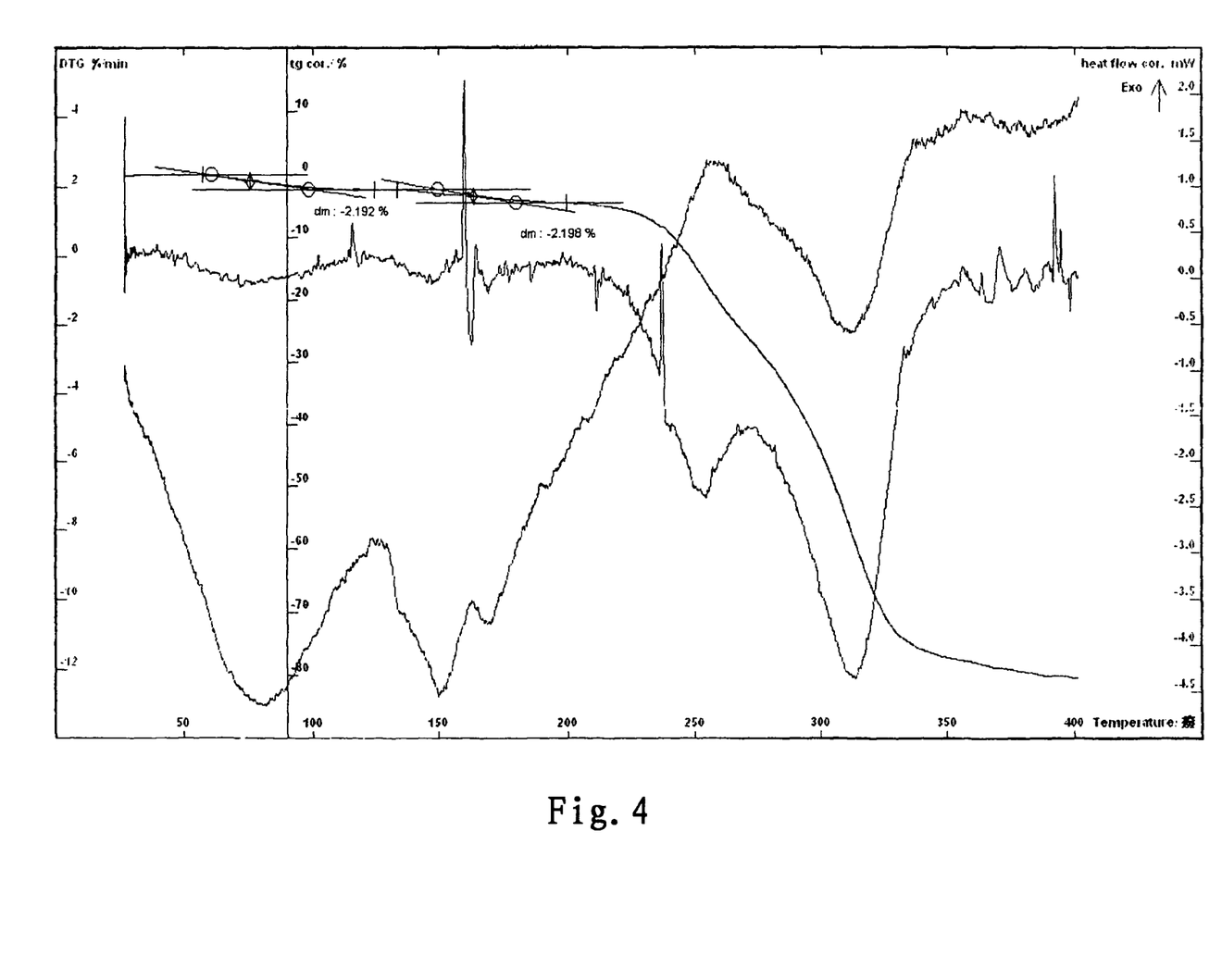
FIG. 4 is a thermogram of erythromycin lactobionate trihydrate.

Lactobionic acid and erythromycin 10 g in a molar ratio (1:1) were added into a reaction bottle, added with water, stirred and dissolved while maintaining the temperature at 5-40° C. After complete reaction, 1 ml of the resultant mixture was filled in each of 20 ml bottles, and cooled to −50° C. for 0.5-6 h. The condenser temperature was cooled to −55° C., vacuumized, and then the temperature was elevated increasingly by a shelf to about −16° C. The mixture was kept for about 28 h at about −16° C., and the temperature was further elevated to about 30° C. and kept for about 10 h to obtain an off-white powder having a yield of 99%. The obtained sample was very freely soluble in water. HPLC: the main peak of the sample had a retention time in consistent with that of erythromycin control; melting point: 137.2-138.7° C. (not corrected); water content by Karl Fischer method was 4.67% (the theoretical value: 4.72%), TG-DTA: weight loss before 200° C. was about 4.39%, which was in the error range of the sample containing 3 crystal water (see FIG. 4), MS (ESI, FAB) m/z: 1092, 1091, 734, 733, 358, 357. The obtained sample was dissolved in water, added with a sodium carbonate solution to generate a precipitate, the precipitate was washed with water, recrystallized from water-ethanol, and the product was consistent with raw material erythromycin in terms of specific optical rotation and MS data. Element analysis: found: C, 51.21%; H, 8.43%, N, 1.17%; calculated: C, 51.34%; H, 8.35%; N, 1.22%.

Example 4

Preparation of Erythromycin Lactobionate Pentahydrate

Figure 3:
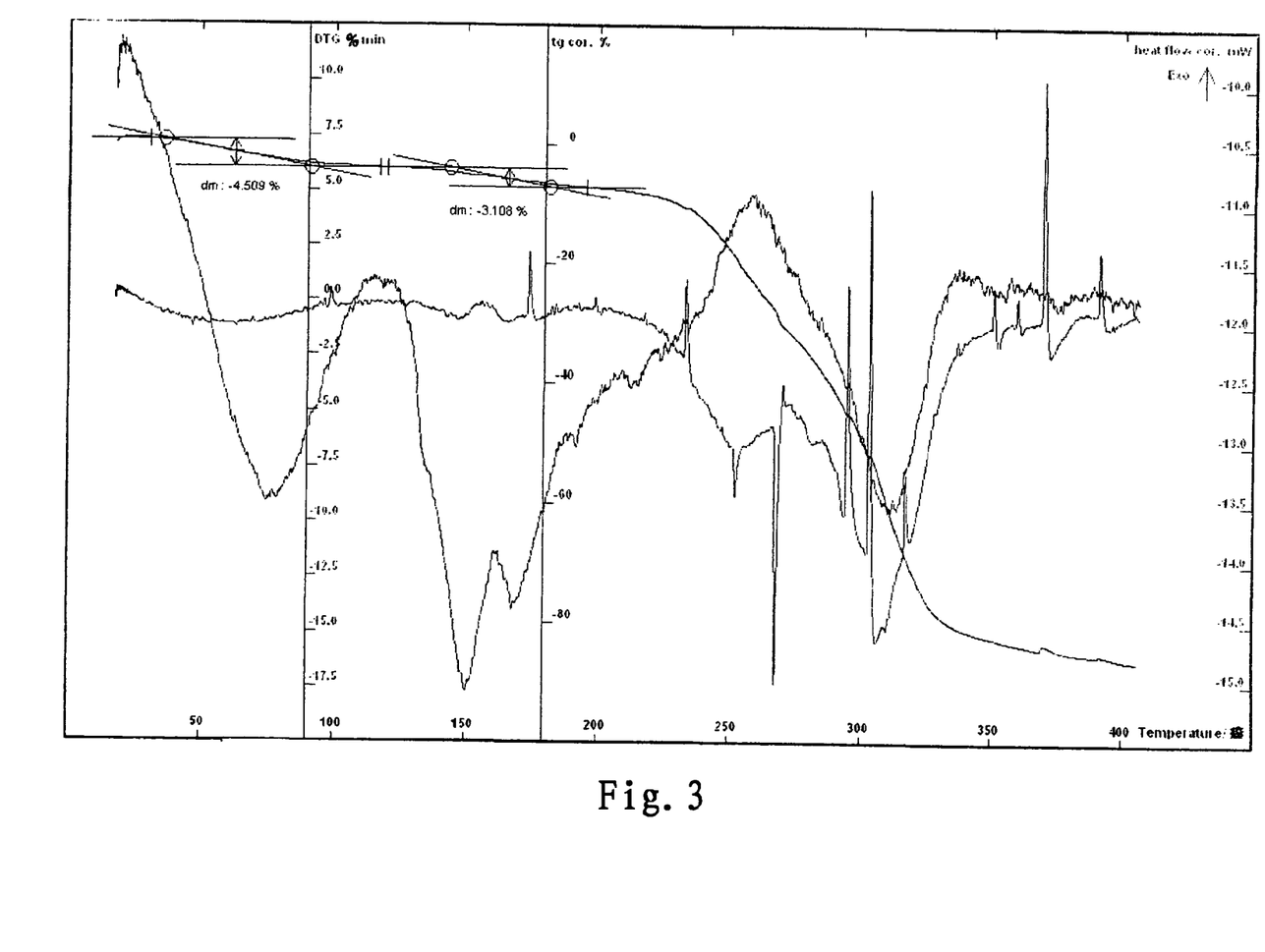
FIG. 3 is a thermogram of erythromycin lactobionate pentahydrate.

In a three-necked flask, 50 ml of anhydrous acetone and 12 g erythromycin were added, dissolved, then added with equimolar lactobionic acid aqueous solution to erythromycin, and continuously stirred at 10-60° C. After complete reaction, 60-400 ml of anhydrous acetone was added slowly. The mixture was cooled to a temperature between −45° C. and −10° C. After filtration, the resultant solid was washed with acetone or chloroform, filtered under a reduced pressure and dried under vacuum at 80° C. for about 4-10 h to obtain an off-white crystal powder, which was very freely soluble in water. HPLC analysis: the main peak of the sample had a retention time in consistent with that of erythromycin control, in which the content of erythromycin was 61.78% (the theoretical value: 62.08%); melting point: 142.2-145.9° C. (not corrected), water content by Karl Fischer method was 7.68% (the theoretical value: 7.62%), TG-DTA: weight loss before 200° C. was about 7.62%, which was in the error range of the sample with 5 crystal water (see FIG. 3), MS (ESI, FAB) m/z: 1092, 1091, 734, 733, 358, 357; Element analysis: found: C, 49.66; H, 8.57; N, 1.12; calculated: C, 49.78; H, 8.44; N, 1.18. The obtained sample was added to a sodium carbonate solution to generate a precipitate, the precipitate was washed with water, recrystallized from water-ethanol, and the product was consistent with raw material erythromycin in terms of specific optical rotation and MS data.

Example 5

Preparation of Erythromycin Lactobionate Hemihepta(3.5)Hydrate

In a three-necked flask, 12 g erythromycin was added and added with acetone to make it dissolved, then added with equimolar lactobionic acid aqueous solution to erythromycin, and continuously stirred at 0-30° C. After complete reaction, 60-400 ml of anhydrous acetone was added slowly. The mixture was cooled to a temperature between −45° C. and −10° C. After filtration, the resultant solid was washed with acetone or chloroform, filtered under a reduced pressure and dried under vacuum at 100° C. for about 4 h to obtain an off-white crystal powder, which was very freely soluble in water. HPLC analysis: the main peak of the sample had a retention time in consistent with that of erythromycin control, in which the content of erythromycin was 63.07% (the theoretical value: 63.53%); melting point: 159.0-161.2° C. (not corrected), water content measured by Karl Fischer method was 5.62% (the theoretical value: 5.46%), TG-DTA: weight loss before 200° C. was about 5.36%, which was in the error range of the sample with 3.5 crystal water, MS (ESI, FAB) m/z: 1092, 1091, 734, 733, 358, 357; Element analysis: found: C, 50.82; H, 8.52; N, 1.13; calculated: C, 50.94; H, 8.38; N, 1.21. The obtained sample was added to a sodium bicarbonate solution to generate a precipitate, the precipitate was washed with water, recrystallized from water-ethanol, and the product was consistent with raw material erythromycin in term of MS data.

Example 6

Preparation of Erythromycin Thiocyanate Trihydrate

Figure 5:
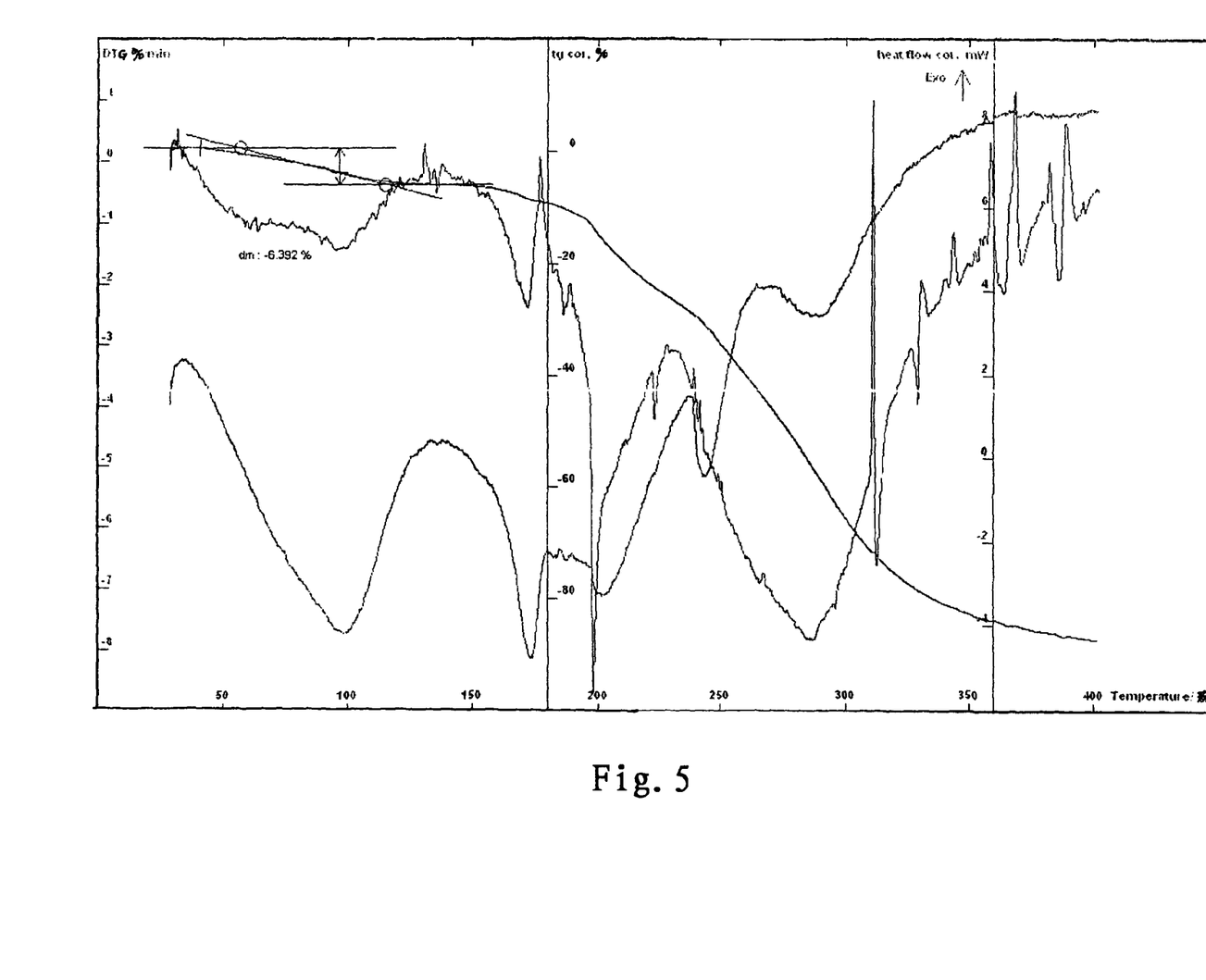
FIG. 5 is a thermogram of erythromycin thiocyanate trihydrate.

In a three-necked flask, 50 ml of water and 10 g erythromycin were added and stirred, then added with equimolar 2M lactic acid aqueous solution to erythromycin, and stirred at 5-40° C. After complete reaction, the mixture was filtered, 10% sodium thiocyanate solution in a molar ratio to erythromycin of 1:1-1.2 was added dropwise, cooled to a temperature between −15° C. and 10° C., the resultant solid was washed with water, filtered under a reduced pressure and dried at room temperature for 48 h to obtain an off-white crystal powder. HPLC analysis: the main peak of the sample had a retention time in consistent with that of erythromycin control, in which the content of erythromycin was 86.61% (the theoretical value: 86.65%); melting point: 161.9-165.1° C. (not corrected), water content measured by Karl Fischer method was 6.42% (the theoretical value: 6.38%), thermogram TG-DTA: weight loss before 140° C. was about 6.39%, which was in the error range of the sample with 3 crystal water (see FIG. 5), MS (ESI, FAB) m/z: 793, 792, 734, 733, 59, 58. Element analysis: found: C, 53.95; H, 8.88; N, 3.39; S, 3.70; calculated: C, 53.88; H, 8.81; N, 3.31; S, 3.79.

Example 7

Preparation of Erythromycin Thiocyanate Dehydrate

Figure 6:
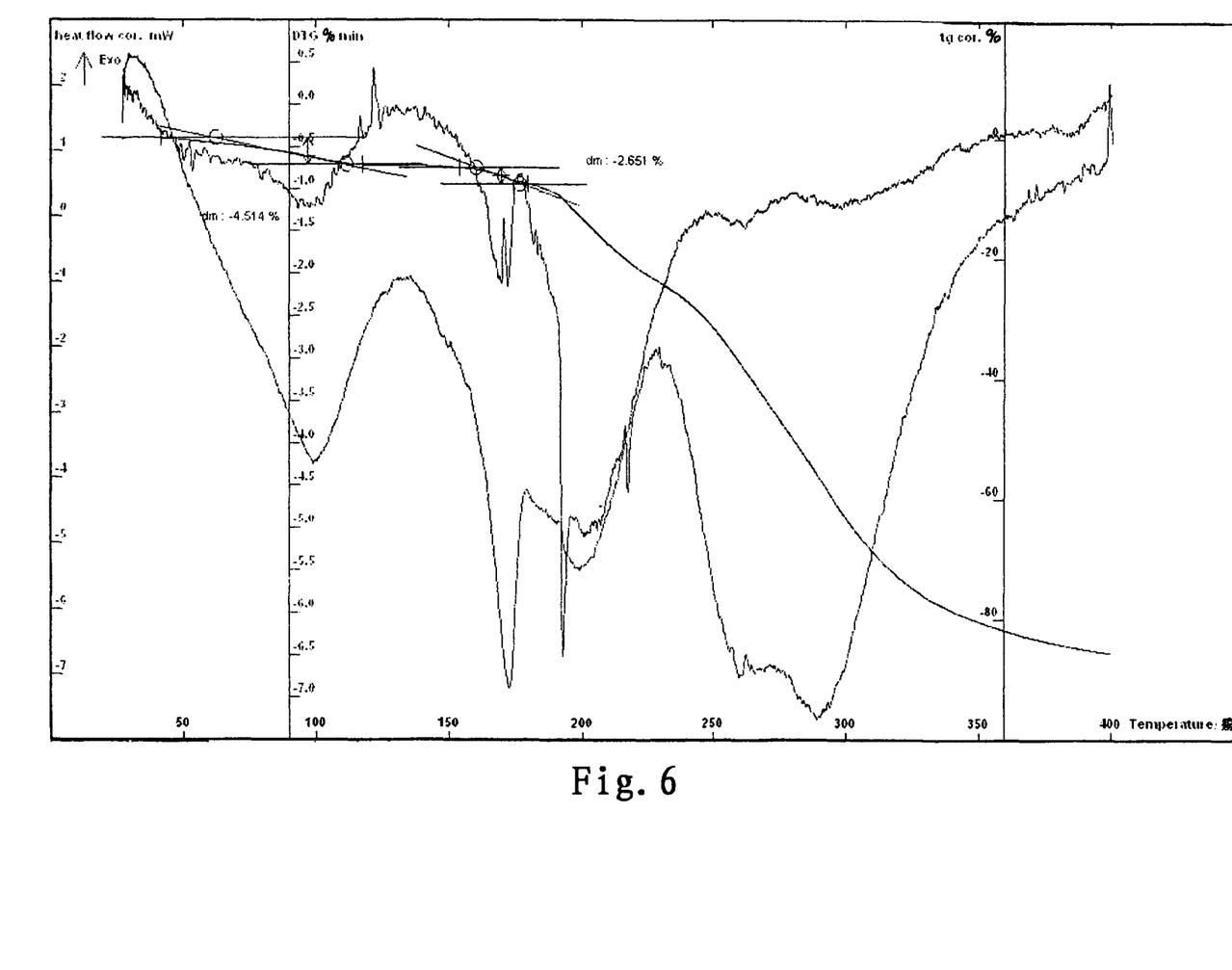
FIG. 6 is a thermogram of erythromycin thiocyanate dihydrate.

In a three-necked flask, 12 g of erythromycin was dissolved in butyl acetate or acetone, added with 2M acetic acid aqueous solution and 10% sodium thiocyanate solution (in a molar ratio to erythromycin of 1:1:1-1.2), and stirred continuously at 15-60° C. After complete reaction, the mixture was added with water, cooled to a temperature between −25° C. and 10° C., filtered, the resultant solid was washed with water, filtered under a reduced pressure, and dried at 60° C. for about 4 h to obtain an off-white crystal powder. HPLC analysis: the main peak of the sample had a retention time in consistent with that of erythromycin control, in which the content of erythromycin was 88.46% (the theoretical value: 88.54%); melting point: 165.8-169.8° C. (not corrected), water content by Karl Fischer method was 4.62% (the theoretical value: 4.35%), TG-DTG: weight loss before 140° C. was about 4.51%, which was in the error range of the sample having 2 crystal water (see FIG. 6), MS (ESI, FAB) m/z: 793, 792, 734, 733, 59, 58. Element analysis: found: C, 54.93; H, 8.87; N, 3.29; S, 3.76; calculated: C, 55.05; H, 8.75; N, 3.38; S, 3.87. The obtained sample having 2 crystal water was added to a sodium carbonate solution to generate a precipitate, the precipitate was washed with water, recrystallized from water-ethanol, and the product was consistent with raw material erythromycin in terms of specific optical rotation and MS data.

Example 8

Preparation of Erythromycin Thiocyanate Hemitri(1.5)Hydrate

Figure 7:
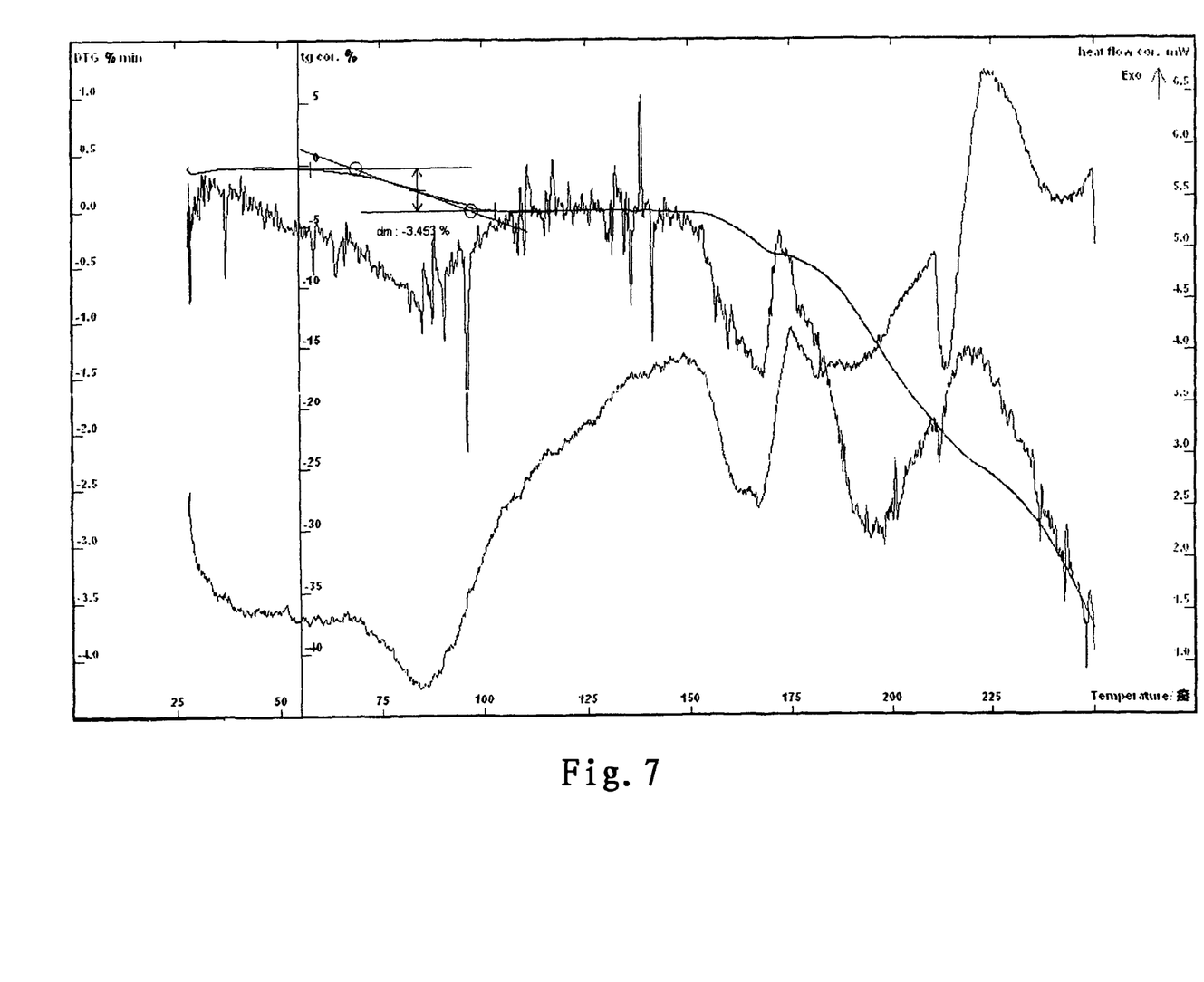
FIG. 7 is a thermogram of erythromycin thiocyanate hemitri(1.5)hydrate.

In a three-necked flask, 0.02 mol of erythromycin and 20 ml of water was added, suspended, and added with 2M acetic acid aqueous solution at 0-30° C. with stirring to make the suspension to be clear. The mixture was filtered, and the filtrate was slowly added dropwise with a solution of 2M sodium thiocyanate or ammonium thiocyanate (in a molar ratio to erythromycin of 1-1.2) with stirring, cooled to a temperature between −10° C. and 10° C., filtered, the resultant solid was washed with water, and filtered under a reduced pressure. The resultant solid was dissolved in methanol, added with 60 ml of water, cooled to a temperature between −15° C. and 10° C. until complete crystallization and precipitation, and dried under vacuum at 60° C. for about 3 h to obtain an off-white crystal powder. HPLC analysis: the main peak of the sample had a retention time in consistent with that of erythromycin control, in which the content of erythromycin was 89.66% (the theoretical value: 89.51%); melting point: 162.4-165.7° C. (not corrected), water content by Karl Fischer method was 3.47% (the theoretical value: 3.30%), TG-DTA: weight loss before 125° C. was about 3.45%, which was in the error range of the sample with 1.5 crystal water (see FIG. 7), MS (ESI, FAB) m/z: 793, 792, 734, 733, 59, 58. IR(KBr) (cm$^{-1}$) 3400-3600(b, s), 978(s), 2879(s), 2046(s), 1681(s), 1467(s), 1380(s), 1175(s), 1095(s); Element analysis: found: C, 55.58; H, 8.82; N, 3.35; S, 3.84; calculated: C, 55.66; H, 8.73; N, 3.42; S, 3.91.

Example 9

Preparation of Erythromycin Lactobionate Hexahydrate

20% Lactobionic acid solution was added dropwise to a reaction container containing erythromycin and water in a molar ratio, the mixture was stirred, and the temperature was controlled between −2° C. and 10° C. The reaction was performed for 0.5-4 h with the pH controlled at 6.4-7, decolored with activated carbon or filtered by an ultrafilter membrane, spray dried with an inlet temperature of 103-115° C., an outlet temperature of 78-88° C. and a spray pressure of 1.1-1.3 kg/cm$^2$ to obtain erythromycin lactobionate hexahydrate.

Example 10

Preparation of Erythromycin Lactobionate Hemihepta(3.5)Hydrate

20% Lactobionic acid solution was added dropwise to a reaction container containing 20 kg of erythromycin, 100 L of water, and 10 L of acetone in a molar ratio. The mixture was stirred with the temperature controlled at 0-10° C., reacted for 1-8 h with the pH controlled at 6.4-7, decolored with activated carbon or filtered by an ultrafilter membrane, spray dried with an inlet temperature of 108-120° C., an outlet temperature of 80-90° C. and a spray pressure of 1.2-1.5 kg/cm$^2$ to obtain erythromycin lactobionate pentahydrate; melting point: 139.6-143.7° C. (not corrected), HPLC analysis: the main peak of the sample had a retention time in consistent with that of erythromycin control; potency: 626 u/mg, pH=7.0, water content by Karl Fischer method was 7.72% (the theoretical value: 7.62%), TG-DTA spectrum: weight loss before 198° C. was about 7.856%, which was in the error range of the sample with 5 crystal water (see FIG. 3), MS (ESI, FAB) m/z: 1092, 1091, 734, 733, 358, 357; the sample was dried at about 100° C. for about 4 h to obtain erythromycin lactobionate hemihepta(3.5)hydrate. The obtained sample was dissolved in water, added with a saturated sodium carbonate solution to generate a precipitate, the precipitate was washed with water, recrystallized from water-ethanol, and the product was consistent with raw material erythromycin in term of MS data.

Example 11

Preparation of Lyophilized Powders of Erythromycin Lactobionate Hydrate

20 Kg of an erythromycin lactobionate hydrate (based on erythromycin) was added with 0-5 Kg of xylitol and 700-1000 L of fresh water for injection, and the mixture was stirred and dissolved. The pH value was measured, and if the pH was 5.0-7.0, no regulation was needed, if the pH was outside this range, 1M NaH$_2$PO$_4$ and 1M Na$_2$HPO$_4$ were added to reach a pH of 5.0-7.0. The mixture was added with activated carbon 0.01-0.5% (WN), stirred for 15-45 min, filtered, supplemented with water to reach 800-1200 L, filtered with 0.22 nm micropore filtration membrane or an ultrafilter membrane with a relative molecular weight cut-off of 1,000-8,000, and filled in 62.5 mg/bottle or 125 mg/bottle (based on erythromycin), lyophilized, plugged to obtain the product.

Example 12

Preparation of Injections of Erythromycin Lactobionate Hydrate

An aseptic erythromycin lactobionate hydrate or erythromycin citrate hydrate or erythromycin phosphate hydrate 25 Kg (based on erythromycin) was weighed, and filled in 125 mg/bottle or 250 mg/bottle or 500 mg/bottle (based on erythromycin) by an aseptic filing process. The bottle was plugged and covered with an aluminum cap to obtain product.

Example 13

Preparation of Erythromycin Thiocyanate Hydrate Tablets

Tablets of erythromycin thiocyanate dihydrate or erythromycin lactobionate trihydrate (250 mg/tablet, based on erythromycin)
Formula:

| | |
|---|---|
| Erythromycin thiocyanate dihydrate or erythromycin lactobionate trihydrate | 250 g (based on erythromycin) |
| Microcrystalline cellulose | 200 g |
| Sodium carboxymethyl starch | 20 g |
| Aspartame | 2 g |
| Polyvinylpyrrolidinone 5% | q.s. |
| Magnesium stearate | 2 g |

Erythromycin thiocyanate dihydrate or erythromycin lactobionate trihydrate, microcrystalline cellulose, sodium carboxymethyl starch, and aspartame were passed through a 100 mesh sieve, processed with 5% polyvinylpyrrolidinone to obtain a soft material, and the material was passed through a 18-24 mesh sieve to form granules. The granules were dried, passed through a 14-20 mesh sieve, finished, added with micronized silica gel and magnesium stearate, mixed and tabletted.

Example 14

Preparation of Erythromycin Lactobionate Trihydrate Capsule

Formula:

| | |
|---|---|
| Erythromycin lactobionate trihydrate | 125 g (based on erythromycin) |
| Microcrystalline cellulose | 100 g |
| Lactose | 20 g |
| Gelatinized starch, 10% | q.s. |
| Magnesium stearate | 2 g |

Erythromycin lactobionate trihydrate, microcrystalline cellulose, and lactose were passed through a 100 mesh sieve, processed with 10% gelatinized starch to form a soft material, and the material was passed through a 18-24 mesh sieve to form granules. The granules were dried, passed through a 14-20 mesh sieve, finished, added with magnesium stearate, mixed and filled in capsules (125 mg/capsule, based on erythromycin).

Example 15

Preparation of Erythromycin Salt Hydrate Granules

Granules of erythromycin lactobionate hydrate or erythromyin lactate hydrate or erythromycin nicotinate hydrate or erythromycin citrate hydrate or erythromycin thiocyanate hydrate (125 mg/packet, based on erythromycin) and the like are prepared as follows.
Formula:

| | |
|---|---|
| A hydrate of organic acid salts of erythromycin | 125 g (based on erythromycin) |
| Mannitol | 100 g |
| Lactose | 20 g |
| Sodium cyclamate | 2 g |
| Solid edible flavor | 1 g |
| Polyvinylpyrrolidinone, 5% | q.s. |

The hydrate of organic acid salt of erythromycin, mannitol, lactose, sodium cyclamate, and solid edible flavor were passed through a 100 mesh sieve, and processed with 5% polyvinylpyrrolidinone to form a soft material. The material was passed through a 18-24 mesh sieve, dried at a temperature of below 60° C., passed through a 14-20 mesh sieve, finished, and filled.

Example 16

Preparation of Erythromycin Salt Hydrate Suppository

A suppository of erythromycin lactobionate hydrate of erythromycin lactate hydrate or erythromycin nicotinate hydrate or erythromycin citrate hydrate or erythromycin thiocyanate hydrate and the like is prepared as follows.
Formula:

| | |
|---|---|
| Hydrate of organic acid salts of erythromycin | 25 g (based on erythromycin, or 100 suppositories) |
| Polyethylene glycol 4000 | 80 g |
| Propylene glycol | 60 ml |
| Poloxamer | 80 g |
| Water | 100 ml |

Glycerol, polyethylene glycol 4000, poloxamer, and propylene glycol were mixed. The mixture was heated in a water bath, stirred to be melt, added with the hydrate of organic acid salts of erythromycin, stirred uniformly, poured rapidly into a suppository mould previously coated with a lubricant until slightly overflowing, smoothed after cooling, and the mould was remove to obtain the product.

Example 17

Preparation of Erythromycin Lactobionate Hydrate Gel

Formula:

| | |
|---|---|
| erythromycin lactobionate hydrate | 25 g (based on erythromycin) |
| Polyethylene glycol 6000 | 50 g |
| Polyethylene glycol 400 | 10 g |

-continued

| | |
|---|---|
| Glycerol | 5 ml |
| Carbomer 934 | 8 g |
| Carbomer 1342 | 2 g |
| Water | 400-500 ml |

Carbomer 1342 and Carbomer 934 were dispersed into water separately, added with glycerol, polyethylene glycol 6,000 and polyethylene glycol 400, stirred and mixed, added with erythromycin lactobionate hydrate, heated, stirred uniformly, added with $Na_2HPO_4$ and $NaH_2PO_4$ solution to adjust the pH to about 5.0-7.0, and filled to obtain the product (250 mg/dose, based on erythromycin).

Example 18

Preparation of Erythromycin a Oxime Thiocyanate and Erythromycin Oxime 20 ml anhydrous methanol and 9 g hydroxyamine hydrochloride were added to a 250 ml three-necked flask at room temperature. The mixture was slowly added portionwise with 7.8 g ammonium bicarbonate with stirring, added with 20 g erythromycin A thiocyanate hydrate (based on the anhydrous), keeping the temperature at 40-80° C. and the pH at 6-7, reacted for 10-40 h, cooled to −10-10° C., filtered, the resultant filter cake with 40-60 ml ice-water twice, dried in an oven to obtain 16 g of product, mp: 160° C. (decomposition). 15 g isopropanol and 8 g erythromycin A oxime thiocyanate were added into a 100 ml three-necked flask at room temperature. The mixture was stirred with the temperature kept at 40-70° C., added dropwise with ammonia to keep the pH at 9.5-12, stirred for 30-90 min, added with 50 ml water, cooled to 0-15° C., stirred for 0.5-1 h, filtered, and dried to obtain 6.2 g of product with a yield of 83%, erythromycin A (E) oxime content of 92%, and melting point: 154-157° C.

Example 19

Thermogravimetry of the Erythromycin Salt Hydrates of the Present Invention

Method and conditions: Setsys 16 from Setaram Company, temperature increasing rate: 10K/min, $N_2$ flow rate: 50 ml/min, room temperature to about 400° C., and the sample amount of about 5 mg.

Example 20

Measurement of Water Content of the Erythromycin Salt Hydrates of the Present Invention Measurement method: water content was measured by the Karl Fischer's method according to China Pharmacopoeia 2005 Edition (CP2005).

What is claimed is:
1. A hydrate of an erythromycin salt selected from the group consisting of:
erythromycin lactobionate undecahydrate having a molecular formula of $C_{37}H_{67}NO_{13}.A.nH_2O$, wherein A is lactobionic acid, and n=11;
erythromycin lactobionate hexahydrate having a molecular formula of $C_{37}H_{67}NO_{13}.A.nH_2O$, wherein A is lactobionic acid, and n=6;
erythromycin lactobionate pentahydrate having a molecular formula of $C_{37}H_{67}NO_{13}.A.nH_2O$, wherein A is lactobionic acid, and n=5;
erythromycin lactobionate hemihepta(3.5)hydrate having a molecular formula of $C_{37}H_{67}NO_{13}.A.nH_2O$, wherein A is lactobionic acid, and n=3.5;
erythromycin lactobionate trihydrate having a molecular formula of $C_{37}H_{67}NO_{13}.A.nH_2O$, wherein A is lactobionic acid, and n=3;
erythromycin thiocyanate trihydrate having a molecular formula of $C_{37}H_{67}NO_{13}.A.nH_2O$, wherein A is thiocyanic acid, and n=3;
erythromycin thiocyanate dihydrate having a molecular formula of $C_{37}H_{67}NO_{13}.A.nH_2O$, wherein A is thiocyanic acid, and n=2; and
erythromycin thiocyanate hemitri(1.5)hydrate having a molecular formula of $C_{37}H_{67}NO_{13}.A.nH_2O$, wherein A is thiocyanic acid, and n=1.5.

2. The hydrate of erythromycin salt according to claim 1, which is erythromycin lactobionate undecahydrate having a molecular formula of $C_{37}H_{67}NO_{13}.A.nH_2O$, wherein A is lactobionic acid, and n=11.

3. The hydrate of erythromycin salt according to claim 1, which is erythromycin lactobionate hexahydrate having a molecular formula of $C_{37}H_{67}NO_{13}.A.nH_2O$, wherein A is lactobionic acid, and n=6.

4. The A hydrate of erythromycin salt according to claim 1, which is erythromycin lactobionate pentahydrate having a molecular formula of $C_{37}H_{67}NO_{13}.A.nH_2O$, wherein A is lactobionic acid, and n=5.

5. The hydrate of erythromycin salt according to claim 1, which is erythromycin lactobionate hemihepta(3.5)hydrate having a molecular formula of $C_{37}H_{67}NO_{13}.A.nH_2O$, wherein A is lactobionic acid, and n=3.5.

6. The hydrate of erythromycin salt according to claim 1, which is erythromycin lactobionate trihydrate having a molecular formula of $C_{37}H_{67}NO_{13}.A.nH_2O$, wherein A is lactobionic acid, and n=3.

7. The hydrate of erythromycin salt according to claim 1, which is erythromycin thiocyanate trihydrate having a molecular formula of $C_{37}H_{67}NO_{13}.A.nH_2O$, wherein A is thiocyanic acid, and n=3.

8. The hydrate of erythromycin salt according to claim 1, which is erythromycin thiocyanate dihydrate having a molecular formula of $C_{37}H_{67}NO_{13}.A.nH_2O$, wherein A is thiocyanic acid, and n=2.

9. The hydrate of erythromycin salt according to claim 1, which is erythromycin thiocyanate hemitri(1.5)hydrate having a molecular formula of $C_{37}H_{67}NO_{13}.A.nH_2O$, wherein A is thiocyanic acid, and n=1.5.

10. A pharmaceutical composition, comprising a hydrate of erythromycin salt according to claim 1 and at least one pharmaceutically acceptable excipient wherein the pharmaceutical composition is formulated into tablets, capsules, powders, or granules.

11. A process for preparing a hydrate of erythromycin salt according to claim 1, comprising:
in a reaction container, using one of chloroform, $C_3$-$C_6$ ketone, $C_2$-$C_6$ ester, water and $C_1$-$C_5$ alcohol and a mixture thereof as solvents, adding erythromycin, stirring, adding lactobionic acid or thiocyanic acid, adding one or more of $C_3$-$C_6$ ketone, chloroform, $C_1$-$C_5$ alcohol, $C_2$-$C_6$ ether, $C_2$-$C_6$ ester and benzene after complete reaction, cooling, filtering, washing the resultant solid with one or more organic solvents of $C_1$-$C_5$ alcohol, $C_3$-$C_6$ ketone, $C_2$-$C_6$ ether and chloroform, filtering under a reduced pressure, and drying to obtain the hydrate of erythromycin salt.

12. A process for preparing a hydrate of erythromycin salt according to claim 1, comprising:

adding lactobionic acid or thiocyanic acid solution in a desired molar ratio into a reaction container containing erythromycin and one or more of water, $C_1$-$C_5$ alcohol and $C_3$-$C_6$ ketone as the solvents, stirring, reacting at a temperature between −10° C. and 30° C. for 0.5-24 h, decoloring with activated carbon or filtering with an ultrafilter membrane after complete reaction, cooling to a temperature between −70° C. and −30° C., and drying under vacuum to obtain the hydrate of erythromycin salt.

13. A process for preparing a hydrate of erythromycin salt according to claim 1, comprising:

adding lactobionic acid or thiocyanic acid or a solution thereof in a desired molar ration into a reaction container containing erythromycin and water, stirring, reacting at a temperature between −5° C. and 20° C. for 0.5-24 h, decoloring with activated carbon or filtering with an ultrafilter membrane after complete reaction, and spray drying to obtain the hydrate of erythromycin salts.

\* \* \* \* \*

UNITED STATES PATENT AND TRADEMARK OFFICE
CERTIFICATE OF CORRECTION

PATENT NO. : 8,470,787 B2
APPLICATION NO. : 13/003397
DATED : June 25, 2013
INVENTOR(S) : Li Liu Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 230 days.

Signed and Sealed this
Eighth Day of September, 2015

Michelle K. Lee
*Director of the United States Patent and Trademark Office*